| United States Patent [19] | [11] | 4,107,077 |
|---|---|---|
| Sullivan, Jr. et al. | [45] | Aug. 15, 1978 |

[54] LIMULUS LYSATE OF IMPROVED SENSITIVITY AND PREPARING THE SAME

[75] Inventors: James D. Sullivan, Jr.; Stanley W. Watson, both of Falmouth, Mass.

[73] Assignee: Associates of Cape Cod, Inc., Woods Hole, Mass.

[21] Appl. No.: 824,226

[22] Filed: Aug. 12, 1977

Related U.S. Application Data

[63] Continuation of Ser. No. 595,800, Jul. 14, 1975, abandoned.

[51] Int. Cl.$^2$ .............. C09K 3/00; G01N 31/00; C12K 1/00
[52] U.S. Cl. .............. 252/408; 23/230 B; 195/103.5 R; 424/2; 424/12; 424/95; 424/101
[58] Field of Search .............. 252/408; 23/230 B; 195/103.5 R; 424/2, 12, 95, 101

[56] References Cited

U.S. PATENT DOCUMENTS

| 3,915,805 | 10/1975 | Levin .............. 195/103.5 R |
| 3,944,391 | 3/1976 | Harris et al. .............. 23/230 B |
| 3,954,663 | 5/1976 | Yamamoto et al. .............. 252/408 |
| 4,038,029 | 7/1977 | Teller et al. .............. 23/230 B |
| 4,038,147 | 7/1977 | Reno .............. 195/103.5 R |

OTHER PUBLICATIONS

Yin, E., et al., Biochim. Biophys. Acta., vol. 261, pp. 284–289 (1972).
Hochstein, D., et al., Bull. Parenteral Drug Assc., vol. 27, No. 3, pp. 139–148 (1973).
Young, N., et al., J. Clin. Invest., vol. 51, pp. 1790–1797 (1972).
Nachum, R., et al., N. Engl. J. Med., vol. 289, pp. 931–934 (1973).

*Primary Examiner*—Benjamin R. Padgett
*Assistant Examiner*—T. S. Gron
*Attorney, Agent, or Firm*—Oblon, Fisher, Spivak, McClelland & Maier

[57] ABSTRACT

Limulus lysate of improved sensitivity to endotoxin is prepared by withdrawing hemolymph from Limulus polyphemus (horseshoe crab), preparing a lysate by lysing the amoebocytes obtained from the hemolymph, treating the lysate with an amount of an organic solvent sufficient to precipitate a clotting inhibitor within the lysate and isolating the organic solvent treated lysate. In another embodiment, the sensitivity of the lysate is further increased by adding a salt of calcium, magnesium, manganese, thereto.

10 Claims, No Drawings

LIMULUS LYSATE OF IMPROVED SENSITIVITY AND PREPARING THE SAME

This is a continuation, of application Ser. No. 595,800, filed Jul. 14, 1975, now abandoned.

BACKGROUND OF THE INVENTION

1. Field of the Invention

The present invention relates to the reaction between Limulus lysate and endotoxins produced from Gram-negative bacteria as a means for detecting Gram-negative bacteria. More particularly, the present invention relates to a Limulus lysate of substantially improved sensitivity for detecting smaller amounts of endotoxins prepared by treating a lysate with an inhibitor denaturing or precipitating solvent.

2. Description of the Prior Art

Endotoxins are lipopolysaccharides, which are found in the outermost cell wall layer of Gram-negative bacteria. The toxins are not present in Gram-positive bacteria. Endotoxins are heat stable and therefore not easily destroyed. They also elicit a variety of symptoms in human beings and other animals with a range of severity which is typified by high fever and frequently death. Endotoxins are present in almost everything we eat, drink or touch. It is fortunate indeed that endotoxins are not toxic until they enter the bloodstream where as little as $10^{-6}$ gm of endotoxin can produce toxic manifestations and even death.

Because endotoxins are so common, they present special problems as far as drug manufacturers are concerned in the manufacture of drugs which are injected intravenously. Quality control is essential to ensure that endotoxins are not present in the medicinal agents produced. Currently, the rabbit fever test is used to test for the endotoxins, but the test has many disadvantages in that it is expensive, time-consuming, not specific, and is only qualitative.

Against this background was the discovery by Levin and Bang (Bull Johns Hopkins Hosp. 115, 265–274) that a lysate isolated by the extraction of the amoebocytes from *Limulus polyphemus,* otherwise known as the horseshoe crab, provides a very sensitive means for detecting the presence of endotoxins in materials. When the lysate contacts an endotoxin containing source, a clot forms which is indicative of the presence of endotoxin. The test has been found to be able to detect as little as $10^{-12}$ gm of endotoxin.

Since the discovery of the ability of Limulus lysate to detect the presence of Gram-negative bacteria or endotoxins, several investigations have been reported concerning the scope of Limulus lysate applicability. Nachum, et al, *New England J. of Medicine,* 289(18), 931 employed the lysate for the detection of Gram-negative bacterial meningitis. The test was found to be superior to such conventional methods as the gram stain and the nitroblue tetrazolium dye test. Both of the conventional methods present numerous technical difficulties and their sensitivity is not satisfactory. Nachum, et al. also were able to substantiate that the Limulus lysate test is inapplicable to the detection of Gram-positive bacterial meningitis, tuberculous meningitis, aseptic meningitis and meningeal leukemia.

Jorgensen, et al, *Applied Microbiology,* 26(1), 1973, 38–42 applied the Limulus lysate test for the detection of endotoxin in children suspected of having Gram-negative bacteriuria. The Limulus test was found to be more sensitive than other conventional tests for the detection of Gram-negative bacteria.

Despite the fact that earlier investigative work has shown the Limulus lysate test to be the most effective diagnostic test to date for the detection of endotoxin derived from Gram-negative bacteria, problems exist with the test in that the sensitivity of the test is widely variable. For instance, Levin, *New England J. Medicine,* 24, 1973(1297–1298), has indicated that because of the variable sensitivity of the Limulus test, problems remain with respect to technique and standardization of the test. Indeed, a detailed study by Jorgensen, et al, *Applied Microbiology,* 26(1), 1973, 43–48, has shown that the potency of Limulus lysate varies widely depending upon the time of year the hemolymph is obtained from the crab for the production of a lysate. For instance, lysate quality appeared diminished in samples prepared in 1972 compared to samples prepared in 1971. The tests of some lysate batches against endotoxin derived from *E. coli* showed a maximum sensitivity for detecting a minimum of 1 ng/ml of endotoxin, while other batches were incapable of detecting as much as 10 ng/ml of endotoxin. It was postulated that the observed variability of the lysate tests probably resulted from biological variations within the amoebocytes which occurred at various "seasons" of the year.

It is therefore readily apparent that despite the proven applicability of the Limulus lysate test for the rapid detection of endotoxins, a need continues to exist for a method of continuously obtaining Limulus lysate under conditions such that the variability of the potency of the individual batches can be controlled and the sensitivity increased.

SUMMARY OF THE INVENTION

Accordingly, one object of the present invention is to provide a Limulus lysate of improved sensitivity for the detection of Gram-negative bacterial endotoxins.

Another object of the present invention is to provide a method of preparing Limulus lysate having improved and controlled sensitivity for the detection of endotoxins.

Yet another object of the present invention is to provide a method of detecting endotoxins in very small amounts with a Limulus lysate of improved sensitivity.

Briefly, these objects and other objects of the invention, as hereinafter will become more readily apparent, can be obtained by a Limulus lysate formed by withdrawing hemolymph from *Limulus polyphemus,* or the horseshoe crab, preparing a lysate by lysing the amoebocytes obtained from the hemolymph, treating the lysate with an organic solvent in amounts sufficient to precipitate a clotting inhibitor in the lysate and isolating the organic solvent treated lysate. In another embodiment of the invention, the sensitivity of the lysate to endotoxin is increased by adding a salt of calcium, manganese, magnesium, to the inhibitor-free lysate.

DETAILED DESCRIPTION OF THE PREFERRED EMBODIMENTS

The improvement of the present process resides in the treatment of Limulus lysate with a solvent which functions to denature and remove a substance from the lysate, hereinafter referred to as the inhibitor. Once the inhibitor is removed from the lysate, the activity of the lysate substantially increases.

The raw material for the lysate produced by the present process is the blood or hemolymph of *Limulus poly-*

*phemus,* also known as the horseshoe crab. Normally, from about 100–200 ml of blood is withdrawn from a crab by inserting a needle into the cardiac chamber of the crab by way of the dorsal junction of the cephalothorax.

The hemolymph from the crab is collected in appropriate sterile containers which have been freed of pyrogen which is a fever-producing substance of bacterial origin. The containers contain a combination of ingredients whose function is to prevent aggregation of the cells as well as to prevent premature lysis of the cells. The ingredients are an aqueous saline solution, normally of about 3% NaCl containing N-ethylmaleimide and usually a buffer. The amount of maleimide used is usually greater than 0.1%, normally about 0.125%. The aqueous solution is usually adjusted to a pH of 6 – 7.4, normally about 7.4 either with or without the presence of a buffer. Normally, the buffer used is Tris (hydroxymethyl)-aminomethane (Tris). When added, the buffer is used in amounts sufficient to adjust the pH to about 7.4. Incidentally, other suitable saline solutions include aqueous KCl solutions. Normally, the temperature of the saline solution ranges from room temperature to about 37° C. The amoebocytes, which are the only formed elements in the hemolymph, are then separated, usually by centrifugation. The blue supernatant is then discarded, and the amoebocytes are then transferred into sterile, pyrogen-free containers.

The lysate is prepared by subjecting the amoebocytes to osmotic lysis by treating the blood cells with pyrogen-free distilled water in a ratio of cells to lysing solution of 1 : 3 – 1 : 6. Other procedures for lysing the amoebocytes include homogenization in which the cells are broken mechanically and freeze-thawing in which the cells are subjected to osmotic lysis with distilled water or by use of a buffered solution at a pH of about 7.4.

In another embodiment for the collection of amoebocytes from the hemolymph of the horseshoe crab, Limulus blood or hemolymph is withdrawn into ice cold, sterile centrifuge tubes and the cells are recovered by low-speed centrifugation, normally about 600 xg. Thereafter, the cells are washed several times with approximately 3% NaCl or KCl, and lysed with distilled, pyrogen-free water wherein the ratio of lysing solution to cells ranges from 3 : 1 – 6 : 1. The lysate can then be isolated from the cellular debris as previously described. Additional lysate can be obtained by re-extracting the cellular debris with pyrogen-free distilled water using about half the initial volume used for lysis.

In yet another embodiment for the collection of amoebocytes, the procedure as described in the preceding paragraph is followed with the exception that after the cells are washed with the saline solution, the cells are lyophilized for future use. When the use of the cells is desired, it is only necessary to add an appropriate amount of distilled water to a given quantity of the freeze-dried cells to promote lysis. Of the three methods described for isolating the amoebocytes and preparing the lysate, the maleimide method is preferred. The cellulose debris from the lysis of the cells is then separated, usually by centrifugation, and discarded, and the supernatant lysate is obtained.

Samples of Limulus lysate were prepared at various times of the year. The wide variability of the activity of the lysate was demonstrated by the fact that 90% of the lysate prepared in the summer of 1972 formed a firm gel with 0.1 to 1.0 ng of endotoxin per ml. Yet, in the summers of 1973 and 1974, very little of the lysate would clot with this range of endotoxin. Further, lysate prepared during the winter of 1973 did not even form a gel with 100 ng of endotoxin.

The essence of the present invention is the discovery that the wide variations in sensitivity of the lysate to endotoxin can be greatly reduced and the sensitivity improved by treating the lysate with certain solvents which function to remove an inhibitor from the lysate. When the lysate is treated with the denaturing solvent, a white precipitate forms at the solvent-lysate interface. Normally, an inhibitor removing amount of from 1 part by volume of denaturing solvent is added to 1 to 2 parts by volume of the lysate. Especially preferred is the combination of 2 volumes of lysate per volume of solvent. Suitable solvents include chloroform, iodoform, bromoform, loweralkyl halides such as methyl bromide, methyl chloride, methyl iodide, ethyl chloride, ethyl bromide, ethyl iodide, propyl chloride, propyl bromide and propyl iodide; ethylene dichloride, methylene dichloride, monohalobenzenes such as chlorobenzene, bromobenzene and iodobenzene; lower alkyl ethers such as dimethyl ether and diethyl ether; carbon tetrachloride, trichloroethylene, toluene and hexane. Normally, highly polar solvents such as dimethylformamide, dimethyl sulfoxide and dimethyl sulfide do not denature the inhibitor in the lysate as well as hydrophilic solvents such as methanol, ethanol, acetone and the like. More specifically, lysate extracted with isoamyl alcohol, phenethyl alcohol, amyl acetate, methyl isobutyl ketone, dichlorobenzene or benzaldehyde does not clot when contacted with a solution containing 1 ng/ml of endotoxin. The order of effectiveness of some of the preferred solvents for denaturing the inhibitor is as follows: chloroform>ethylenedichloride>methylenedichloride>ethyl ether>carbon tetrachloride->trichloroethylene>toluene>hexane. Most preferred solvents include chloroform, ethylene chloride, and methylene chloride. The extraction process is normally accomplished at 0° to 5° C, preferably 5° C. The extracted lysate exhibits an increase of ten-to-one hundred fold in sensitivity over non-extracted lysate.

The lysate is extracted by thoroughly mixing the lysate and organic solvent by any convenient method such as by vortexing at temperatures not exceeding 5° C for not more than several hours. After mixing, the insoluble phases are separated and the precipitated inhibitor-solvent material is allowed to settle. It is helpful to centrifuge the phases to facilitate separation of the lysate solvent mixture. After separation, the aqueous phase is withdrawn and stored at cold temperatures sufficient to ensure stability of the lysate, usually $-20°$ to $-74°$ C until it can be freeze-dried. The sooner the lysate is stored, the better the activity of the lysate can be ensured.

The stability of the lysate is effected by the solvent extraction. For instance, when chloroform is used as the extracting solvent, the activity of the lysate can decrease when stored at $-74°$ C as early as from three to six months after preparation. Non-extracted lysate, on the other hand, can be stored for periods up to one year at $-74°$ C without loss of activity. In fact, non-extracted lysate is typically stable for more than one week at 5° C. Chloroform extracted lysate, on the other hand, is unstable at room temperature and frequently loses activity when stored overnight at 5° C. Because of the instability problem, the extracted lysate is stored in ice when used in daily measurements. If the extracted lysate is lyophilized, its stability is greatly improved and, in fact, its stability surpasses that of non-extracted lysate. The lysate can be lyophilized by dispensing a volume of the lysate, usually about 5 ml into a container, such as a serum vial. The dispensed lysate is then frozen, usually at very low temperatures such as $-74°$ C, and thereafter lyophilized under a vacuum ranging from 5 - 20 $\mu$m. The containers are then sealed after drying under a vacuum, and thereafter stored at $-74°$ C. The lyophilized lysate has been stored for more than 12 months without loss of activity, and has even been found to be stable at 37° C for 2 months.

The nature of the inhibitor which is denatured or precipitated by the process of the invention is not absolutely understood; however, preliminary indications seem to suggest that it is a lipoprotein. Polyacrylamide disc gel electrophoresis of the lysate both before and after solvent extraction indicates the disappearance of a protein band which is stainable with Sudan black (a lipoprotein stain); after extraction with solvent. Gel samples of extracted lysate and non-extracted lysate, when stained with Coomassie blue, which is a general protein stain, did not show a difference in protein pattern. The presence of many proteins in the gel could mask the staining of inhibitor with Coomassie blue.

The in vivo role of the inhibitor in the crab is not known. It may possibly enter into one or more of the sequence of steps which lead to clotting of Limulus's blood which is known in some detail. The clotting mechanism includes activation of an enzyme by the presence of endotoxin followed by enzymatic conversion of the clottable protein present in the blood to a gel. It is believed that possibly the inhibitor in the lysate may function by reacting with endotoxin and thus at least partially neutralizing or tying up the endotoxin which consequently decreases the lysates sensitivity. Seasonal fluctuations in the amount of inhibitor relative to the other clotting components of Limulus's blood may very well account for the variable sensitivity of the lysate derived from the crab. An interesting corrolary would seem to exist with human blood in that it has been observed that human blood contains a protein which reversibly binds endotoxin, thus interfering with the detection of endotoxin already present in human blood or which has been added thereto. If human serum or plasma containing endotoxin is extracted with chloroform, the presence of the endotoxin can be detected by the lysate. The inhibitors of both human blood and Limulus blood are both sensitive to chloroform, which suggests, in view of the facts above, that both may function to bind endotoxin. Another plausible explanation for the function of the inhibitor is that it may interfere with the action of the endotoxin activated enzyme on the clottable protein. An observation which lends credence to this supposition is the finding that trypsin in the absence of endotoxin gels the lysate or purified clottable protein. The trypsin inhibitor will block the trypsin-catalyzed reaction, but will not block the endotoxin-dependent reaction. These facts would seem to suggest that the clotting enzyme in the lysate or blood is similar to trypsin in its role in the overall clotting mechanism, and that it is controlled by an inhibitor highly specific like the trypsin inhibitor.

In another embodiment of the invention, the sensitivity of the extracted lysate can further be increased by the addition of a divalent metal cation to the lysate. Suitable divalent metal compounds include the halides of manganese and the alkaline earth metals such as $CaCl_2$, $MgCl_2$ and the like. Normally, the lysate is treated with a 0.02 M to 0.2 M solution of the salt, preferably a 0.02 M to 0.05 M solution. Preferred salts are the chlorides of calcium, magnesium and manganese. The precise manner in which the cations function to increase the sensitivity of the lysate is not known. It may be that the cation acts in a significant manner during any one of several steps such as the enzyme activation step in conjunction with the endotoxin, the reaction of the activated enzyme with clottable protein or the polymerization step which results in a gel.

The presence of the divalent cation in the lysate also counteracts the inhibiting effect of saline solution when the lysate (solvent extracted or unextracted) is used in conjunction with a saline solution in a test. The increased sensitivity of the divalent cation-containing lysate can be appreciated by reference to Table 1.

TABLE 1.

Effect of Chloroform Extraction and Addition of Salts on Lysate Sensitivity

| Treatment of lysate | Endotoxin (ng/ml) required for clot formation* |
|---|---|
| Before chloroform extraction | |
| No added salts | 6 |
| 0.02 M $CaCl_2$ and 0.154 M NaCl added | 1 |
| After chloroform extraction | |
| No added salts | 1 |
| 0.02 M $CaCl_2$ and 0.154 M NaCl added | 0.04 |

*Results typical for lysate prepared during summer of 1974.

It is evident from the data in Table 1 that the sensitivity of not only the extracted lysate is improved by the presence of certain divalent metal cations, but also the sensitivity of non-extracted lysate. The apparent ability of saline solutions to influence the sensitivity of the lysate to endotoxin clearly suggests that the sensitivity of the lysate can be carefully regulated by adding whatever amount of saline solution necessary to obtain a given sensitivity for the lysate. This ability to regulate the sensitivity of the lysate is another embodiment of the present invention.

The improved lysate of the present invention exhibits a sensitivity for endotoxin of 50 - 100 times that of the conventional lysates which have not been extracted with a denaturing or precipitating solvent. Previously, the limit of sensitivity of the non-extracted lysate was about $10^{-10}$ grams of endotoxin. With the improvement of the present invention, the sensitivity limit has now been extended to about $1 - 5 \times 10^{-12}$ gms of endotoxin.

In addition to the use of the lysate of the present invention for the detection of endotoxin in human body fluids, the lysate can also be used to detect the presence of Gram-negative bacteria in other sources. For instance, the lysate can be used in conjunction with other parameters to determine the bacterial level of seawater with regard to the vertical and horizontal distribution of bacteria in seawater, thus providing a means of measuring the pollution of natural bodies of water with organic material.

Limulus lysate is sensitive to the endotoxins released from all Gram-negative bacteria which include, for example, the species of *pseudomonas, salmonella,* and *escherichia.*

Having generally described the invention, a further understanding can be obtained by reference to certain specific examples which are provided herein for purposes of illustration only and are not intended to be limiting unless otherwise specified.

PREPARATION OF LIMULUS LYSATE

Horseshoe crabs were obtained from the Woods Hole Marine Biological Laboratory. The crabs were bled three to five times per week, and fifty crabs were bled at any given time to obtain a pool of blood. The crabs were bled by inserting a 13-gauge needle into the cardiac chambers by way of the dorsal junction of the cephalothorax, and the hemolymph obtained was collected in sterile, pyrogen-free siliconized 250 ml glass centrifuge bottles containing 125 ml of 0.125% N-ethylmaleimide dissolved in pyrogen-free 3% sodium chloride which was optionally adjusted to a pH of 7.4 immediately before use with tris(hydroxymethyl)-aminomethane buffer and warmed to 42° C. The amoebocytes were obtained from the collected hemolymph by centrifuging the same at 500 xg for 10 minutes. The blue supernatant fluid was discarded, and the packed amoebocytes were transferred to pyrogen-free siliconized 50 ml glass centrifuge tubes and washed twice with pyrogen-free 3% NaCl to remove the N-ethylmaleimide. The cells were then lysed by adding pyrogen-free distilled water (Travenol) at a 1:3 to 1:6 ratio of cells to water. The suspension was thoroughly mixed in a Vortex Genie mixer and allowed to stand at 4° C for 18 to 24 hours. The cellular debris was removed by centrifuging at 500–800 xg for 10 minutes, and the lysate was decanted and stored in pyrogen-free vials at $-20°$ C, or for shorter periods of time at 4° C in Erlenmeyer flasks.

ASSAY OF THE LYSATE AND PREPARATION OF STANDARD ENDOTOXIN SOLUTIONS

The sensitivity of all lysate samples was measured by mixing 0.1 ml of lysate with 0.1 ml of endotoxin in a pyrogen-free disposable 10 × 75 mm test tube. The mixture was incubated at 37° C for 1 hour, and the test was scored as positive if the lysate formed a clot which would not break when the tube was slowly inverted 180°.

Standard solutions of 1 ng/ml endotoxin were freshly prepared from a stock solution of endotoxin stored at 5° C each day with pyrogen-free water. This fresh solution was used to prepare a diluted series of endotoxin solutions. The stock solution was prepared from a *Klebsiella pneumoniae* standard endotoxin preparation furnished by the Food and Drug Administration. The solution contained 100 ng/ml of endotoxin when reconstituted with 10 ml of pyrogen-free distilled water. Other endotoxin standards used were solutions of *Escherichia coli* 0127: B8 (Difco) and *Salmonella minnesota* 9700 (Difco).

SOLVENT REMOVAL OF INHIBITOR FROM LYSATE

Equal volumes of lysate and organic solvents were shaken for 20 min. to 1 hour on a rotary shaker at 5° C. After shaking, the mixture was centrifuged (4,000 xg) and the aqueous phase was withdrawn or decanted and titered with various concentrations of endotoxin. All solvents used were reagent grade and appeared free of endotoxins.

EXAMPLE A

A series of three lysate samples of 5–10 ml volume were combined with the same volume of chloroform. Each mixture was vortexed and centrifuged at 15–20 min. (8,000 rpm). In each case, the upper aqueous layer was withdrawn from the tube and tested with standard endotoxin solution, i.e., 0.2 ml of endotoxin (1 ng/ml or less) with 0.15 ml lysate. The results indicated that all three chloroform extracted lysate samples gave a clot in 60 minutes or less under the same conditions, while the same lysate samples which were not extracted with chloroform, exhibited no clotting.

EXAMPLE B

A 20 ml sample of lysate was added to a 10 ml of chloroform (2:1 v/v ratio) and the mixture was vortexed and then centrifuged at 8000 rpm. The recovered aqueous phase was stored in 5 ml aliquots at various temperatures as shown in the table below. A 0.15 ml sample of each aliquot was mixed with 0.2 ml of 1 ng/ml endotoxin solution and the absence or presence of a clot was observed.

| Storage Temperature | Solution Appearance | Clot Formation* (0→4) |
|---|---|---|
| Lyophilized sample frozen in liq. $N_2$ | Clear | 4 |
| 5° C | Clear | 4 |
| $-20°$ C | Slightly turbid | 2 |
| $-74°$ C | Clear | 4 |
| Non-extracted lysate | Clear | 0 |

*The notation (0→4) indicates a scale used in grading the clots which form and is defined as follows:
4+ firm gel of considerable opacity
3+ soft gel with moderate to considerable opacity
2+ weak gel with slight to moderate opacity. Also, starch-like floccules adhere to sides of the tube when tube is slanted.
1+ very weak gel with slight opacity with some starch-like floccules adhering to sides of tube.
0 no visible increase in viscosity or opacity.

EXAMPLE C

Samples of lysate were extracted by the various solvents shown in Table 2 below according to the procedure of Example B and were tested for endotoxin sensitivity. The sensitivities of the various extracted lysate samples are also shown in the table.

TABLE 2

| Extraction solvent | Titer after solvent extraction (ng/ml of endotoxin needed for clot formation) |
|---|---|
| Chloroform | 0.08 |
| Ethylene chloride | 0.2 |
| Methylene chloride | 0.2 |
| Ethyl ether | 0.4 |
| Carbon tetrachloride | 0.6 |
| Trichloroethylene | 0.6 |
| N-hexane | 1.0 |
| Toluene | 1.0 |

LYOPHILIZATION AND STORAGE OF LYSATE

Before lyophilizing, 5 ml of lysate was dispensed into 10-ml serum vials equipped with a split rubber stopper. The lysate was then frozen at $-74°$ C, lyophilized, and sealed under 10-μm vacuum in a Virtis 10–800 freeze-dryer (Gardiner, N.Y.) equipped with a stoppering plate. Usually, 99 vials of lysate were dried at a time with a drying time of approximately 36 h. The moisture content of dried lysate was 2%. After drying, the vials were banded with metal seals and stored at $-74°$ C.

BIOCHEMICAL STUDIES ON LIMULUS LYSATE

A problem which has been studied to some extent once the properties of Limulus lysate were appreciated, is the identification and characterization of the high molecular weight protein (believed to be an enzyme) responsible for the activation of the low molecular weight clotting protein. As a first step in the identification process, the low and high molecular weight fractions of the lysate were isolated as follows: The lysate was reacted with endotoxin at 37° C for 60 minutes, whereby a gel formed. The gel was broken and then centrifuged. The supernatant liquid was collected. This liquid contained the clotting enzyme, while, on the other hand, the precipitate consisted of the polymerized clotting protein. The addition of further amounts of endotoxin to the enzyme fraction (supernatant) did not result in further gelation indicating that the reaction had gone to completion and that no clottable protein remained in the supernatant.

The supernatant fraction containing the clotting enzyme was partially purified on DEAE-cellulose by ion exchange chromatography. A solution containing the enzyme after equilibration by dialysis against 0.02 M ammonium acetate at pH 6.5 was applied to a 2.5 cm X 5 cm column of DEAE-cellulose which had been previously washed with the same buffer. By this treatment the enzyme was absorbed on the cellulose and extraneous protein was elected from the column by addition of further ammonium acetate buffer (less than 0.1 M) of appropriate pH. After sufficient washing with buffer solution, the enzyme was eluted from the column with 0.1 M ammonium acetate buffer. Thereafter, the column was washed with ammonium acetate solutions of 0.25 molar and 0.5 molar to elute additional protein which exhibited no clotting enzyme activity. The enzyme eluted from the column did not lose activity by this treatment. The enzyme obtained by the ion exchange treatment was then further purified by gel filtration on Sephadex G-100 and the purity of the enzyme was determined by disc gel electrophoresis. It was found that if the enzyme is subjected to a pH less than 3 or if it is heated for 60 minutes at 60° C, the enzyme irreversibly loses activity.

When Limulus lysate was fractionated on a column of Sephadex G-100 (2.5 cm × 60 cm), four major fractions were obtained. The column had been eluted with 0.1 M ammonium acetate at a pH of 7 at 5° C, and no effort was spared to avoid endotoxin contamination of all apparatus used. Of the fractions isolated, only peaks I and III formed a firm gel which formed without additional endotoxin.

The observed formation of gel when fractions I and III were combined suggests that either some residual amounts of endotoxin were present which caused gel formation, or else the inhibitor was removed which resulted in the formation of the gel. If the latter interpretation is correct, the inhibitor must be present in the lysate to prevent spontaneous clotting of the lysate. It is also possible that the presence of endotoxin inactivates the inhibitor, and it would logically seem to follow that the sensitivity of the lysate to endotoxin would be controlled by the amount of inhibitor present.

ECOLOGICAL STUDIES

Because natural bodies of water such as seawater contain bacteria, a study was conducted using Limulus lysate as a means for detecting Gram-negative bacteria. Bacteria are an integral part of the biological cycle in the ocean and are primarily responsible for the mineralization of organic matter in the oceans. The rate of mineralization of the seawater to a large extent influences the primary productivity of the oceans and therefore, indirectly influences the amount of protein which can be harvested from the oceans for human consumption. Because the conventional methods of counting bacteria in the oceans have been less than satisfactory, it was believed that the Limulus lysate could provide an effective means for measuring the bacterial distribution in oceans.

Since the Limulus lysate test is responsive to as little as $10^{-12}$ gms of endotoxin, and since the dry weight of endotoxins (lipopolysaccharides) is about $10^{-14}$ gm derived from a single bacterium of $E.\ coli,$ for instance, weighing about $10^{-13}$ gm, it is apparent that the Limulus test can detect as few as 100 bacteria. In view of this information, the analysis of seawater for endotoxin was attempted. A one liter amount of seawater was filtered through a 0.2 μ Millipore filter, and the filter was boiled for five minutes and sonicated for 10 minutes to free the endotoxins from the filter. The sonicated medium was then titered for endotoxins by the Limulus test.

This technique was used to achieve an ocean water bacteria profile for two ocean cruisers from Woods Hole, Mass. to Bermuda and from Lisbon, Portugal to the Azores. Water was periodically collected from the surface to a depth of 5000 meters, and the results of the study indicated that over 99% of the ocean bacteria are located in the upper 200 meters of the watercolumn. The upper waters contained from $10^3 - 10^4$ bacteria per ml. The bacteria count diminished at increasing depths, and at depths below 1000 meters there were only 1 – 10 bacteria per ml.

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A method for preparing Limulus lysate of enhanced sensitivity to endotoxin, which comprises:
   withdrawing hemolymph from horseshoe crabs (Limulus);
   preparing a lysate by lysing the amoebocytes obtained from said hemolymph;
   treating said lysate with an amount of an organic solvent selected from the group consisting of chloroform, iodoform, bromoform, methylbromide, methylchloride, methyliodide, ethylchloride, ethylbromide, ethyliodide, propylchloride, propylbromide, propyliodide, ethylene chloride, methylene chloride, chlorobenzene, bromobenzene, iodobenzene, dimethylether, diethylether, carbontetrachloride, trichloroethylene, toluene and hexane sufficient to denature a clotting inhibitor present in said lysate; and
   isolating said organic solvent treated lysate.

2. The method of claim 1, wherein said organic solvent is chloroform, ethylene chloride, methylene chloride, diethylether, carbontetrachloride, trichloroethylene, toluene, or hexane.

3. The method of claim 2, wherein said solvent is chloroform.

4. The method of claim 1, which further comprises: adding a sensitivity increasing amount of a chloride salt of manganese, calcium or magnesium to said organic solvent treated lysate.

5. The method of claim 1, wherein said hemolymph is withdrawn into an aqueous saline solution whose function is to prevent aggregation and premature lysis of the amoebocytes in said hemolymph containing N-ethylmaleimide and the resulting solution is centrifuged, whereby the amoebocytes in said hemolymph are separated, and wherein said separated amoebocytes are lysed and the cellular debris removed from the resulting lysate.

6. The method of claim 1, wherein the volume ratio of solvent to lysate ranges from 1:1 to 2.

7. A method for preparing Limulus lysate of enhanced sensitivity to endotoxin, which comprises the steps of:
   withdrawing hemolymph from horseshoe crabs (Limulus);
   preparing a lysate by lysing the amoebocytes obtained from said hemolymph;
   treating said lysate with an amount of an organic solvent selected from the group consisting of chloroform, iodoform, bromoform, methylbromide, methylchloride, methyliodide, ethylchloride, ethylbromide, ethyliodide, propylchloride, propylbromide, propyliodide, ethylene chloride, methylene chloride, chlorobenzene, bromobenzene, iodobenzene, dimethylether, diethylether, carbontetrachloride, trichloroethylene, toluene and hexane sufficient to denature a clotting inhibitor present in said lysate;
   isolating said organic solvent treated lysate; and
   adding a sensitivity increasing amount of a chloride salt of manganese, calcium or magnesium to said extracted lysate.

8. A lysate sensitive to endotoxins derived from horseshoe crabs (Limulus) by a process comprising:
   withdrawing hemolymph from horseshoe crabs (Limulus);
   preparing a lysate by lysing the amoebocytes obtained from said hemolymph;
   treating said lysate with an amount of an organic solvent selected from the group consisting of chloroform, iodoform, bromoform, methylbromide, methylchloride, methyliodide, ethylchloride, ethylbromide, ethyliodide, propylchloride, propylbromide, propyliodide, ethylenechloride, methylenechloride, chlorobenzene, bromobenzene, iodobenzene, dimethylether, diethylether, carbontetrachloride, trichloroethylene, toluene and hexane sufficient to denature a clotting inhibitor present in said lysate; and
   isolating said organic solvent treated lysate.

9. The lysate of claim 8, wherein said organic solvent is chloroform, ethylene chloride, methylene chloride, diethylether, carbontetrachloride, trichloroethylene, toluene, or hexane.

10. The lysate of claim 8, wherein said lysate of increased sensitivity is obtained by treating said lysate with chloroform.

* * * * *